United States Patent [19]

Diefenbach

[11] Patent Number: 4,698,451
[45] Date of Patent: Oct. 6, 1987

[54] DIRHENIUM METATHESIS CATALYSTS

[75] Inventor: Steven P. Diefenbach, Baton Rouge, La.

[73] Assignee: Ethyl Corporation, Richmond, Va.

[21] Appl. No.: 875,085

[22] Filed: Jun. 17, 1986

[51] Int. Cl.$^4$ .......................... C07C 2/00; B01J 31/00
[52] U.S. Cl. .................................... 585/534; 502/162; 502/169; 502/171; 526/285
[58] Field of Search ........................ 585/534; 526/285; 502/162, 169, 171

[56] References Cited

U.S. PATENT DOCUMENTS

| 4,080,491 | 3/1978 | Kobayashi et al. | 526/124 |
| 4,427,595 | 1/1984 | Schrock | 585/534 |
| 4,465,890 | 8/1984 | Kukes et al. | 585/645 |

OTHER PUBLICATIONS

Mortreux et al., J. Mol. Catal., 1977, 2, 73–82.
Edwards et al., J. Am. Chem. Soc., 1982, 104, 6806–6808.
Barder et al., J. Am. Chem. Soc., 1984, 106, 2882–2891.

Primary Examiner—Curtis R. Davis
Attorney, Agent, or Firm—Donald L. Johnson; John F. Sieberth

[57] ABSTRACT

Described are novel bimetallic complexes particularly useful as homogeneous catalysts for the metathesis of alkynes, and methods for the preparation of such complexes. The complexes are formed from (i) a dirhenium halide having (a) a double or triple bond between a pair of rhenium atoms, and (b) a bis(dihydrocarbylphosphino)alkane coordinated therewith, and (ii) a Group III-A alkoxide in which the alkoxy groups are perfluorinated or are substantially perfluorinated. The complexes can be produced very easily and quickly. All that is required is to establish intimate contact between components (i) and (ii), preferably in an innocuous liquid organic solvent. 3-Heptyne was metathesized in good yields by means of the complex formed from $Re_2Cl_4(dppm)_2$ and $Al(OCH(CH_3)_2)_3$, and the complex formed from $Re_2Cl_6(dppm)_2$ and $Al(OCH(CF_3)_2)_3$ (dppm=bis(diphenylphosphino))methane).

34 Claims, No Drawings

DIRHENIUM METATHESIS CATALYSTS

TECHNICAL FIELD

This invention relates to novel bimetallic complexes particularly useful as homogeneous catalysts for the metathesis of alkynes, to the preparation of such complexes and to the metathesis of acetylenes (alkynes) using such complexes as catalysts.

BACKGROUND

Prior work on homogeneous catalysts for the metathesis of acetylenes is relatively sparse. The first published report on this subject appears to be that of Mortreux, et al., J. Mol. Catal., 1977, 2, 73. Their work involved use of Mo(CO)$_6$.

There is one report by Edwards and Schrock that a rhenium complex, (Re(C-t-bu)(CH-t-bu)(TMEDA)I$_2$, will convert several equivalents of 3-heptyne into 3-hexyne and 4-octyne before metathesis ceases. See *J. Am. Chem. Soc.*, 1982, 104, 6806-8.

THE INVENTION

A new type of bimetallic dirhenium complexes has now been discovered. They consist essentially of a complex formed from (i) a dirhenium halide having (a) a double or triple bond between a pair of rhenium atoms, and (b) a bis(dihydrocarbylphosphino)alkane ligand coordinated therewith, and (ii) a Group III-A fluoroalkoxide. By appropriate selection of the Group III-A fluoroalkoxide, catalysts for catalytically metathesizing a metathesizable acetylene compound are provided. More particularly, acetylenic metathesis may be achieved when component (ii) used in forming the complex is a Group III-A perfluoroalkoxide or a substantially polyfluorinated alkoxide in which the alpha carbon atom contains either one methyl group or one hydrogen atom. Component (ii) preferably contains aluminum as the Group III-A element.

The catalyst compositions of this invention usually can be produced very easily and quickly. All that is required is to establish intimate contact between components (i) and (ii). In some cases use of slightly elevated temperatures is desirable. While this reaction may be performed in bulk (no added solvent) it is preferable to synthesize the compounds of this invention in an innocuous liquid organic solvent. Suitable solvents for synthesis (and for metathesis as well) include aromatic, aliphatic and cycloaliphatic hydrocarbons, fluorocarbons, halogenated aromatic hydrocarbons, relatively unreactive halogenated aliphatic hydrocarbons (e.g., methylene dichloride, ethylene dichloride, etc.), and the like. Ethers such as tetrahydrofuran and nitriles such as butyronitrile tend to destroy the catalytic activity of the complexes in acetylene metathesis. In any given case the suitability of a proposed solvent for the production of the complexes and/or for the metathesis reaction may be readily determined by the expedient of performing a few simple tests utilizing the procedures described in the ensuing examples.

As is well known a variety of acetylenic compounds are metathesizable, including unsymmetrical dialkylacetylenes such as 3-heptyne, 3-octyne, 3-nonyne, 4-nonyne and their higher homologs containing up to about 36 or more carbon atoms; arylacetylenes, such as 1-phenyl-1-butyne, 1-phenyl-2-butyne, 1-(p-tolyl)-2-pentyne, and their higher homologs containing up to about 40 or more carbon atoms, and the like. It is also well known that mixtures of suitable metathesizable acetylenic compounds may be cometathesized to produce a product differing from either reactant. A few illustrative mixtures suitable for co-metathesis include 3-hexyne and 4-octyne, 3-heptyne and 5-decyne, and 1,4-diphenyl-2-butyne and 3-hexyne. Preferred acetylenes contain up to about 20 carbon atoms, and most preferably up to about 12 carbon atoms. Naturally when only one acetylenic compound is being metathesized, it should be an unsymmetrical acetylenic compound so that the metathesis product will differ from the initial acetylenic compound. In co-metathesis, symmetrical or unsymmetrical acetylenes may be present in the initial mixture.

When component (i) is composed of a triply bonded dirhenium compound it has the empirical formula:

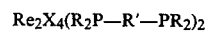

where X is halogen, preferably Cl, R is hydrocarbyl (alkyl, cycloalkyl, cycloalkylalkyl, alkenyl, aryl, aralkyl, etc., any of which may be substituted with halogen atoms), and R' is an alkylene group, preferably containing no more than about three carbon atoms, such as trimethylene, dimethylene, ethylidene, 2,2-propylidene, and most preferably, methylene. The two R groups of either or both of the respective phosphino) groups may be joined together in the form a cyclic ring system such as in a 1,2-dimethylene or 1,3-trimethylene group. R preferably contains up to about 18 carbon atoms, although there is no known reason to consider this as a critical limitation. Rather it simply reflects the kinds of raw materials that are most readily available in the marketplace. A few illustrative compounds include

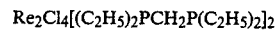

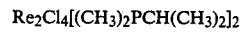

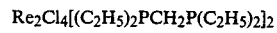

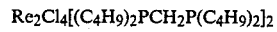

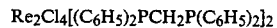

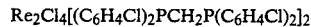

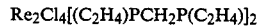

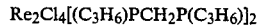

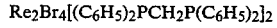

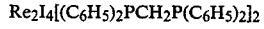

When composed of a doubly bonded dirhenium compound component (i) has the empirical formula: Re$_2$X$_4$(—X)$_2$(R$_2$P—R'—PR$_2$), or, more simply: Re$_2$X$_6$(R$_2$P—R'—PR$_2$)hd 2, where X, R, and R' are as defined above. These compounds are exemplified by the following:

$Re_2Cl_6[(C_2H_5)_2PCH_2CH_2P(C_2H_5)_2]_2$ $Re_2Cl_6[(C_4H_9)_2PCH_2P(C_4H_9)_2]_2$ $Re_2Cl_6[(C_6H_5)_2PCH_2P(C_6H_5)_2]_2$ $Re_2Cl_6[(C_6H_4Cl)_2PCH_2P(C_6H_4Cl)_2]_2$ $Re_2Cl_6[(C_2H_4)PCH_2P(C_2H_4)]_2$ $Re_2Cl_6[(C_3H_6)PCH_2P(C_3H_6)]_2$ $Re_2Cl_6[(C_3H_6)PC(CH_3)_2P(C_3H_6)]_2$ $Re_2Br_6[(C_6H_5)_2PCH_2P(C_6H_5)_2]_2$

Methods suitable for synthesizing the above dirhenium compounds have been reported in the literature. See for example Barder et al., J. Am. Chem. Soc. 1984, 106, 2882–91, the disclosure of which is incorporated herein by reference.

Component (ii), a fluoroalkoxide of a Group III-A element (B, Al, Ga, In, Tl), contains one or two, and preferably three fluoroalkoxy groups. For producing complexes having acetylenic metathesis activity, use should be made of fluoroalkoxides in which the alkoxy groups are perfluorinated or are substantially perfluorinated, i.e., they contain on the alpha carbon either one methyl group or, preferably, one hydrogen atom and the balance of the alkoxy group is perfluorinated. When component (ii) contains less than three perfluorinated or substantially perfluorinated fluoroalkoxy groups, the remaining valence(s) of the Group III-A element may be satisfied by hydrocarbyl groups, phenoxy or alkoxy groups. Thus these compounds may be depicted by the general formula $$M(OR^1)R^2R^3$$

where M is a Group III-A element, preferably aluminum. $R^1$ is a perfluorinated or substantially perfluorinated fluoroalkoxy group (as above defined), and $R^2$ and $R^3$ may be the same or different from each other and are hydrocarbyl, halohydrocarbyl, hydrocarbyloxy or halohydrocarbyloxy groups. Preferably $R^1$, $R^2$ and $R^3$ each contains up to about 18 carbon atoms. Most preferably $R_2$ and $R_3$ are the same as $R_1$. Component (ii) should be capable of complexing with the dirhenium halide compound employed as component (i).

A few illustrative compositions of this invention include the complexes made from:

$Re_2Cl_4[(C_2H_5)_2PCH_2P(C_2H_5)_2]_2$ & $Al(OCF_2CF_3)_3$ $Re_2Cl_4[(CH_3)_2PCH(CH_3)P(CH_3)_2]_2$ & $B(OCH(CF_3)_2)_3$ $Re_2Cl_4[(C_2H_5)_2PCH_2CH_2P(C_2H_5)_2]_2$ & $Al(OCF_2CF_2CF_3)_3$ $Re_2Cl_4[(C_4H_9)_2PCH_2P(C_4H_9)_2]_2$ & $Tl(OCF_2CF_3)_3$ $Re_2Cl_4[(C_6H_5)_2PCH_2P(C_6H_5)_2]_2$ & $Al(OCF_2CF_3)_2(OC_2H_5)$ $Re_2Cl_4[(C_6H_4Cl)_2PCH_2P(C_6H_4Cl)_2]_2$ & $Al(OCH(CF_3)_2)_2(C_6H_5)$ $Re_2Cl_4[(C_2H_4)PCH_2P(C_2H_4)]_2$ & $Al(OCF_3)_3$ $Re_2Cl_4[(C_3H_6)PCH_2P(C_3H_6)_2]_2$ & $Al(OCF_3)(OCF_2CF_3)_2$ $Re_2Cl_4[(C_3H_6)PC(CH_3)_2P(C_3H_6)_2]_2$ & $Al(OCH(CF_3)_2)_3$ $Re_2Br_4[(C_6H_5)_2PCH_2P(C_6H_5)_2]_2$ & $Ga(OCF_3)_3$ $Re_2Cl_6[(C_2H_5)_2PCH_2P(C_2H_5)_2]_2$ & $Al(OCF_2CF_3)_3$ $Re_2Cl_6[(CH_3)_2PCH(CH_3)P(CH_3)_2]_2$ & $Al(OCH(CF_3)_2)_3$ $Re_2Cl_6[(C_2H_5)_2PCH_2CH_2P(C_2H_5)_2]_2$ & $Tl(OCH(CF_3)_2)_3$ $Re_2Cl_6[(C_4H_9)_2PCH_2P(C_4H_9)_2]_2$ & $B(OCF_2CF_3)_3$ $Re_2Cl_6[(C_6H_5)_2PCH_2P(C_6H_5)_2]_2$ & $Al(OCF_2CF_2CF_2CF_3)_3$ $Re_2Cl_6[(C_6H_4Cl)_2PCH_2P(C_6H_4Cl)_2]_2$ & $Al(OCH(CF_3)_2)_3$ $Re_2Cl_6[(C_2H_4)PCH_2P(C_2H_4)]_2$ & $In(OCH(CF_3)_2)_3$ $Re_2Cl_6[(C_3H_6)PCH_2P(C_3H_6)]_2$ & $Tl(OCF_3)_3$ $Re_2Cl_6[(C_3H_6)PCH_2(CH_3)_2P(C_3H_6)]_2$ & $AlOCF_3OCH_3)_2$ $Re_2Br_6[(C_6H_5)_2PCH_2P(C_6H_5)_2]_2$ & $Al(OCH(CF_3)_2)_2CF_3)$

Without desiring to be bound in any way by theoretical considerations, it is believed that during complex formation two of the halogen atoms initially present on the dirhenium halide bis(dihydrocarbylphosphino)alkane coordination compound become displaced by anionic species of the Group III-A fluoroalkoxide. In any event, the result of the interaction between components (i) and (ii) is the formation of a product, deemed a complex, having useful properties, such as the ability to metathesize acetylenic hydrocarbons and as a dopant for use in the manufacture of compound semiconductors and epitaxial coatings therefor.

Accordingly, this invention provides in another of its embodiments the process of producing a complex of (i) a dirhenium halide having (a) a double or triple bond between a pair of rhenium atoms, and (b) a bis(dihydrocarbylphosphino)alkane coordinated therewith, and (ii) a Group III-A fluoroalkoxide which comprises effecting reaction between components (i) and (ii). Preferably the reaction is conducted in an innocuous liquid reaction solvent.

The following examples illustrate the practice of various embodiments of this invention. $Re_2Cl_4(dppm)_2$ and $Re_2Cl_6(dppm)_2$ (dppm=bis(diphenylphosphino))methane) were prepared following the procedures of Barder et al. (loc. cit.). All manipulations were performed under nitrogen or argon by using either Schlenk or dry nitrogen box techniques. Solvents were passed through an alumina column, dried over 4 angstrom molecular sieves, deoxygenated with argon, and stored in the dry box. The acetylenes were obtained from standard sources and were passed through an alumina column, dried over 4 angstrom molecular sieves, and stored in the dry box.

The complexes of this invention were prepared in situ in a two dram vial equipped with a stirring bar by adding one equivalent of triethylaluminum (Ethyl Corporation) to a chlorobenzene ("PhCl") solution of the flouoralkanol, e.g., $(CF_3)_2CHOH$ (Aldrich Chemical Co.). After stirring the mixture at 30° C. for 2-3 hours the appropriate quantity of the dirhenium halide bis(dihydrocarbylphosphino)alkane coordination compound was added followed by addition of the acetylenic compound to be metathesized. The tightly sealed vial was removed from the dry box and placed in an aluminum block heater preset at the desired temperature. Reactions were monitered and products identified by gas chromatography using a Varian 3700 gas chromatograph connected to a Hewlett-Packard 3390A integrator.

The conditions and results of metathesis reactions of this invention using 3-heptyne ("3H") or 1-phenyl-1-butyne ("PB") are summarized in the Table.

TABLE

Synthesis of Complexes and Use in Metathesis Reactions

| Ex. No. | Component (i) (mmoles) | Component (ii) (mmoles) | Alkyne mmoles | Conditions | Percent Metathesis |
|---|---|---|---|---|---|
| 1 | $Re_2Cl_4(dppm)_2$ (.014) | $Al(OCH(CF_3)_2)_3$ (.056) | 3H (1.0) | PhCl/70°/18h | 27 |
| 2 | $Re_2Cl_4(dppm)_2$ (.028) | $Al(OCH(CF_3)_2)_3$ (.112) | 3H (1.0) | PhCl/70°/18 h | 61 |
| 3 | $Re_2Cl_4(dppm)_2$ (.021) | $Al(OCH(CF_3)_2)_3$ (.084) | 3H (1.0) | PhCl/80°/ 4 h | 78 |
| 4 | $Re_2Cl_6(dppm)_2$ (.06) | $Al(OCH(CF_3)_2)_3$ (.06) | 3H (1.0) | PhCl/70°/72 h | 60 |
| 5 | $Re_2Cl_4(dppm)_2$ (.015) | $Al(OCMe(CF_3)_2)_3$ (.06) | 3H (1.0) | PhCl/70°/18 h | 10 |
| 6 | $Re_2Cl_4(dppm)_2$ (.016) | $Al(OCH(CF_3)_2)_3$ (.062) | PB (1.0) | PhCl/70°/18 h | 8 |

The values for the percent metathesis given in the Table were developed as follows: using the vpc area percent data on the reaction products, the sum of the quantities of the products formed was divided by the quantity of the initial acetylenic reactant remaining in the product, and this value was multiplied by 100.

As this invention is susceptible to variation in its practice without departing from its true spirit and scope, it is not intended that this invention be unduly limited to the exemplifications hereinbefore presented. Rather, what is intended to be embodied in the coverage of this invention is as set forth in the ensuing claims and the equivalents thereof.

What is claimed is:

1. A complex formed from (i) a dirhenium halide having (a) a double or triple bond between a pair of rhenium atoms, and (b) a bis(dihydrocarbylphosphino)alkane coordinated therewith, and (ii) a Group III-A alkoxide in which the alkoxy groups are perfluorinated or are substantially perfluorinated.

2. A composition of claim 1 formed from (i) a dirhenium chloride having (a) a double or triple bond between a pair of rhenium atoms, and (b) a bis(dihydrocarbylphosphino)methane coordinated therewith, and (ii) a Group III-A alkoxide in which the alkoxy groups are perfluorinated or are substantially perfluorinated.

3. A composition of claim 1 formed from (i) a dirhenium halide having (a) a triple bond between a pair of rhenium atoms, and (b) the empirical formula $$Re_2X_4L_2$$

where each X is a halogen atom and each L is a coordinated bis(dihydrocarbylphosphino)alkane ligand, and (ii) a Group III-A alkoxide in which the alkoxy groups are perfluorinated or are substantially perfluorinated.

4. A composition of claim 1 formed from (i) a dirhenium halide having (a) a triple bond between a pair of rhenium atoms, and (b) the empirical formula $$Re_2X_4L_2$$

where each X is a halogen atom and each L is a coordinated bis(dihydrocarbylphosphino)alkane ligand, and (ii) an aluminum trialkoxide in which the alkoxy groups are perfluorinated or are substantially perfluorinated.

5. A composition of claim 1 formed from (i) a dirhenium chloride having (a) a triple bond between a pair of rhenium atoms, and (b) the empirical formula $$Re_2Cl_4L_2$$

where each L is a coordinated bis(dihydrocarbylphosphino)methane ligand, and (ii) $Al(OCCH_3(CF_3)_2)_3$.

6. A composition of claim 1 formed from (i) a dirhenium chloride having (a) a triple bond between a pair of rhenium atoms, and (b) the empirical formula $$Re_2Cl_4L_2$$

where each L is bis(diphenylphosphino)methane ligand, and (ii) $Al(OCH(CF_3)_2)_3$.

7. A composition of claim 1 formed from (i) a dirhenium halide having (a) a double bond between a pair of rhenium atoms, and (b) the empirical formula $$Re_2X_6L_2$$

where each X is a halogen atom and each L is a coordinated bis(dihydrocarbylphosphino)alkane ligand, and (ii) a Group III-A alkoxide in which the alkoxy groups are perfluorinated or are substantially perfluorinated.

8. A composition of claim 1 formed from (i) a dirhenium halide having (a) a double bond between a pair of rhenium atoms, and (b) the empirical formula $$Re_2X_6L_2$$

where each X is a halogen atom and each L is a coordinated bis(dihydrocarbylphosphino)alkane ligand, and (ii) an aluminum trialkoxide in which the alkoxy groups are perfluorinated or are substantially perfluorinated.

9. A composition of claim 1 formed from (i) a dirhenium chloride having (a) a double bond between a pair of rhenium atoms, and (b) the empirical formula $$Re_2Cl_6L_2$$

where each L is a coordinated bis(dihydrocarbylphosphino)methane ligand, and (ii) an aluminum trialkoxide in which the alkoxy groups are perfluorinated or are substantially perfluorinated.

10. A composition of claim 1 formed from (i) a dirhenium chloride having (a) a double bond between a pair of rhenium atoms, and (b) the empirical formula $Re_2Cl_6L_2$ where each L is bis(diphenylphosphino)methane ligand, and (ii) $Al(OCH(CF_3)_2)_3$.

11. In a process of catalytically metathesizing a metathesizable acetylene compound, the improvement in which said compound is contacted with a catalyst formed from (i) a dirhenium halide having (a) a double or triple bond between a pair of rhenium atoms, and (b) a bis(dihydrocarbylphosphino)alkane coordinated therewith, and (ii) a Group III-A alkoxide in which the alkoxy groups are perfluorinated or are substantially perfluorinated.

12. A process of claim 11 in which (i) used in forming the catalyst is a dirhenium chloride having (a) a double or triple bond between a pair of rhenium atoms, and (b) a bis(dihydrocarbylphosphino)methane coordinated therewith.

13. A process of claim 11 in which (i) used in forming the catalyst is a dirhenium halide having (a) a triple bond between a pair of rhenium atoms, and (b, the empirical formula $Re_2X_4L_2$ where each X is a halogen atom and each L is a coordinated bis(dihydrocarbylphosphino)alkane ligand.

14. A process of claim 11 in which (i) used in forming the catalyst is a dirhenium chloride having (a) a triple bond between a pair of rhenium atoms, and (b) the empirical formula $Re_2Cl_4L_2$ where each L is a coordinated bis(dihydrocarbylphosphino)methane ligand.

15. A process of claim 11 in which (i) used in forming the catalyst is a dirhenium chloride having (a) a triple bond between a pair of rhenium atoms, and (b) the empirical formula $Re_2Cl_4L_2$ where each L is bis(diphenylphosphino))methane ligand.

16. A process of claim 11 in which (i) used in forming the catalyst is a dirhenium halide having (a) a double bond between a pair of rhenium atoms, and (b) the empirical formula $Re_2X_6L_2$ where each X is a halogen atom and each L is a coordinated bis(dihydrocarbylphosphino)alkane ligand.

17. A process of claim 11 in which (i) used in forming the catalyst is a dirhenium chloride having (a) a double bond between a pair of rhenium atoms, and (b) the empirical formula $Re_2Cl_6L_2$ where each L is a coordinated bis(dihydrocarbylphosphino)methane ligand.

18. A process of claim 11 in which (ii) used in forming the catalyst is an aluminum trialkoxide in which the alkoxy groups are perfluorinated or are substantially perfluorinated.

19. A process of claim 11 in which (ii) used in forming the catalyst is $Al(OCCH_3(CF_3)_2)_3$.

20. A process of claim 11 in which (ii) used in forming the catalyst is $Al(OCH(CF_3)_2)_3$.

21. A process of claim 11 conducted in a liquid reaction medium.

22. A process of claim 11 conducted in a hydrocarbon, perfluorocarbon, or halogenated hydrocarbon reaction medium.

23. A process of claim 11 conducted in a chlorinated hydrocarbon reaction medium.

24. A process of claim 11 conducted in a chlorobenzene or methylene dichloride reaction medium.

25. A process of claim 11 in which (i) used in forming the catalyst is a dirhenium chloride having (a) a triple bond between a pair of rhenium atoms, and (b) the empirical formula $Re_2Cl_4L_2$ where each L is a coordinated bis(dihydrocarbylphosphino)methane ligand, and in which (ii) used in forming the catalyst is an aluminum trialkoxide in which the alkoxy groups are perfluorinated or are substantially perfluorinated.

26. A process of claim 25 in which (ii) used in forming the catalyst is $Al(OCCH_3(CF_3)_2)_3$.

27. A process of claim 25 in which (ii) used in forming the catalyst is $(OCH(CF_3)_2)_3$.

28. A process of claim 11 in which (i) used in forming the catalyst is a dirhenium chloride having (a) a double bond between a pair of rhenium atoms, and (b) the empirical formula $Re_2Cl_6L_2$ where each L is a coordinated bis(dihydrocarbylphosphino)methane ligand, and in which (ii) used in forming the catalyst is an aluminum trialkoxide in which the alkoxy groups are perfluorinated or are substantially perfluorinated.

29. A process of claim 28 in which (ii) used in forming the catalyst is $Al(OCCH_3(CF_3)_2)_3$.

30. A process of claim 28 in which (ii) used in forming the catalyst is $Al(OCH(CF_3)_2)_3$.

31. A process of catalytically metathesizing one or more metathesizable acetylenic compounds which comprises forming a catalyst from (i) a dirhenium halide having (a) a double or triple bond between a pair of rhenium atoms, and (b) a bis(dihydrocarbylphosphino)alkane coordinated therewith, and (ii) a Group III-A alkoxide in which the alkoxy groups are perfluorinated or are substantially perfluorinated, and conducting the metathesis in the presence of the catalyst so that metathesis of the metathesizable acetylenic compound(s) takes place.

32. A process of claim 31 further characterized by both forming said catalyst and conducting said metathesis in a liquid reaction medium.

33. The process of producing a complex of (i) a dirhenium halide having (a) a double or triple bond between a pair of rhenium atoms, and (b) a bis(dihydrocarbylphosphino))alkane coordinated therewith, and (ii) a Group III-A alkoxide which comprises effecting reaction between components (i) and (ii) in a liquid reaction medium so that said complex is formed.

34. A process of claim 33 in which the halide of (i) used in forming the complex is chloride, in which the bis(dihydrocarbylphosphino))alkane of (i) used in forming the complex is a bis(diarylphosphino))methane, and in which (ii) used in forming the complex is $Al(OCH(CF_3)_2)_3$.

* * * * *

UNITED STATES PATENT AND TRADEMARK OFFICE
CERTIFICATE OF CORRECTION

PATENT NO. : 4,698,451

DATED : OCTOBER 6, 1987

INVENTOR(S) : STEVEN P. DIEFENBACH

It is certified that error appears in the above-identified patent and that said Letters Patent is hereby corrected as shown below: Title page:

Abstract, line 15 reads "$Al(OCH(CH_3)_2)_3$" and should read -- $Al(OCH(CF_3)_2)_3)$ --.

Column 1, line 18 reads "(Re(C-t-bu)" and should read -- Re(C-t-bu) --.

Column 2, line 38 reads "$(CH_3)_2]_2$" and should read -- $(CH_3)P(CH_3)_2]_2$ --.

Column 2, line 40 reads "$PCH_2P(C_2H_5)_2]_2$" and should read -- $PCH_2CH_2P(C_2H_5)_2]_2$ --.

Column 2, line 60 reads "$--PR_2)hd 2$" and should read -- $--PR_2)_2$ --.

Column 2, line 65 reads "$PCH_2(CH_3)$" and should read -- $PCH(CH_3)$ --.

Column 3, line 66 reads "$(C_2H_4)_2]_2$" and should read -- $(C_2H_4)]_2$ --.

Column 4, line 1 reads "$(C_3H_6)_2]_2$" and should read -- $(C_3H_6)]_2$ --.

Column 4, line 3 reads "$(C_3H_6)_2]_2$" and should read -- $(C_3H_6)]_2$ --.

UNITED STATES PATENT AND TRADEMARK OFFICE
CERTIFICATE OF CORRECTION

PATENT NO. : 4,698,451

DATED : OCTOBER 6, 1987

INVENTOR(S) : STEVEN P. DIEFENBACH

It is certified that error appears in the above-identified patent and that said Letters Patent is hereby corrected as shown below:

Column 4, line 27 reads "$AlOCF_3OCH_3)_2$" and should read -- $AlOCF_3(OCH_3)_2)$ --.

Column 5, lines 2 and 3 reads "flouoralkanol" and should read -- fluoroalkanol --.

Column 8, line 26 reads "$(OCH(CF_3)_2)_3$" and should read -- $Al(OCH(CF_3)_2)_3$ --.

Signed and Sealed this

Twenty-third Day of February, 1988

Attest:

DONALD J. QUIGG

Attesting Officer     Commissioner of Patents and Trademarks